United States Patent [19]

Longmore

[11] Patent Number: 4,827,931
[45] Date of Patent: May 9, 1989

[54] SURGICAL CATHETERS WITH SUTURING DEVICE AND NMR OPAQUE MATERIAL

[76] Inventor: Donald B. Longmore, 97 Chertsey Lane, Staines, Middlesex, England

[21] Appl. No.: 124,106

[22] PCT Filed: Jan. 13, 1987

[86] PCT No.: PCT/GB87/00014
§ 371 Date: Sep. 23, 1987
§ 102(e) Date: Sep. 23, 1987

[87] PCT Pub. No.: WO87/04080
PCT Pub. Date: Jul. 16, 1987

[30] Foreign Application Priority Data

Jan. 13, 1986 [GB] United Kingdom ............... 8600665

[51] Int. Cl.⁴ .............................................. A61B 17/04
[52] U.S. Cl. .................................... 128/334 R; 128/4; 128/303.1; 128/653
[58] Field of Search ......................................... 128/4–8, 128/303.1, 334 C, 334 R, 335–395–398, 653, 656–658

[56] References Cited

U.S. PATENT DOCUMENTS

| | | | |
|---|---|---|---|
| 3,058,473 | 10/1962 | Whitehead | 128/349 |
| 3,470,876 | 10/1969 | Barchilon | 128/348 |
| 3,847,157 | 11/1974 | Caillouette et al. | 128/348 |
| 4,266,547 | 5/1981 | Kemiya | 128/303.1 |
| 4,418,688 | 12/1983 | Loeb | 128/6 |
| 4,491,135 | 1/1985 | Klein | 128/340 |
| 4,572,198 | 2/1986 | Codrington | 128/653 |
| 4,621,640 | 11/1986 | Mulhollan et al. | 128/334 R |
| 4,669,465 | 6/1987 | Moore et al. | 128/395 |

FOREIGN PATENT DOCUMENTS 0165742 12/1985 European Pat. Off. .
2820239 11/1978 Fed. Rep. of Germany .
WO86/01093 2/1986 World Int. Prop. O. .

Primary Examiner—Max Hindenburg
Attorney, Agent, or Firm—Watson, Cole, Grindle & Watson

[57] ABSTRACT

A surgical catheter for use on a patient undergoing NMR examination is composed of an elongated element made up of axial segments which are composed of materials which alternate from being highly opaque under NMR examination and less opaque under NMR examination, thereby enabling identification of the entire length of the catheter in the NMR field.

6 Claims, 3 Drawing Sheets

SURGICAL CATHETERS WITH SUTURING DEVICE AND NMR OPAQUE MATERIAL

This invention relates to operating catheters for use in surgical procedures.

Catheters in accordance with the invention are characterized in that they are composed of non-magnetic materials which are opaque or translucent under Nuclear Magnetic Resonance (NMR) examination. Suitable materials may be hydron, or strongly paramagnetic materials such as gadolinium. The catheters are preferably of axially segmented construction, having segments of highly opaque material alternating with segments of less opacity, so that the precise location of the catheter is readily apparent under NMR examination and visually at the distal end.

The catheters have, in each case, a main central lumen for the passage, e.g., of optic fibres for laser surgery, or of drugs for perfusion into an organ or into a cancer, or of control elements for the manipulation of surgical instruments carried at the distal end of the catheter.

Additionally, small lumens may be provided through the length of the catheter wall for the passage of guidance wires, or gas, or drugs.

The catheters are preferably coated, internally and externally, with thin layers of silicone rubber.

In each case, these catheters permit the conduct of many operations and treatments which would otherwise be carried out under X-ray. When operations are of long duration or require repetitions, the patient is subjected to undesirable high exposure to X-ray radiation. The present catheters make it possible to conduct various procedures under NMR examination, which is non-invasive and not subject to the risks attendant upon exposure to radiation.

Some catheters in accordance with the invention and attachments for use therewith will now be described by way of example, with reference to the accompanying drawings.

DETAILED DESCRIPTION OF THE PREFERRED EMBODIMENTS

Figure 1:
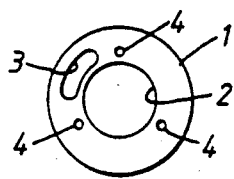
FIG. 1 is a diagrammatic cross-section of a first embodiment of catheter according to the present invention and for use in cancer treatment.
Figure 2:
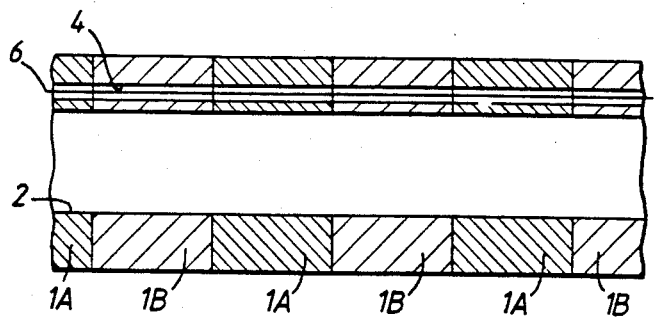
FIG. 2 is an axial section, drawn to a larger scale, of the catheter of FIG. 1.

The catheter 1 of FIGS. 1 and 2 is in the form of an elongated element composed of alternating annular segments 1A, 1B of materials which are highly opaque to NMR examination and less opaque, respectively. The catheter has thin coatings of silicone rubber on its external surface and the internal surface of its main, central lumen 2. For the treatment of cancers, the lumen is charged with a quantity of embolising material which can be selectively discharged through the distal end of the catheter by a plunger (not shown) of NMR opaque material operable from the proximal end of the catheter.

A secondary lumen 3 formed through the wall of the catheter is charged with sclerosing materials. Three equi-spaced fine lumens 4 also extend longitudinally through the catheter wall and form passages for high tensile guide wires 6. At the distal end, these wires are secured to the catheter wall, and at the proximal end they are coupled to a joystick or rollerball control which permits the wires to be selectively and individually tightened or relaxes so as to permit guidance of the distal end of the catheter.

In use of the catheter, embolising material can be selectively discharged into an artery supplying a tumour, or a vein draining it or both. The secondary lumen 3 may be used for the injection of sclerosing materials into the arterial system before embolisation.

Use of the catheter under NMR examination has the additional advantage that the efficacy of embolisation cn be monitored while the treatment is under way by NMR examination of blood flow sequences.

In a modification the catheter may be of simple construction with just a main lumen, for use in the perfusion of tumour-killing drugs which are too toxic to be adminstered systematically.

Figure 3:
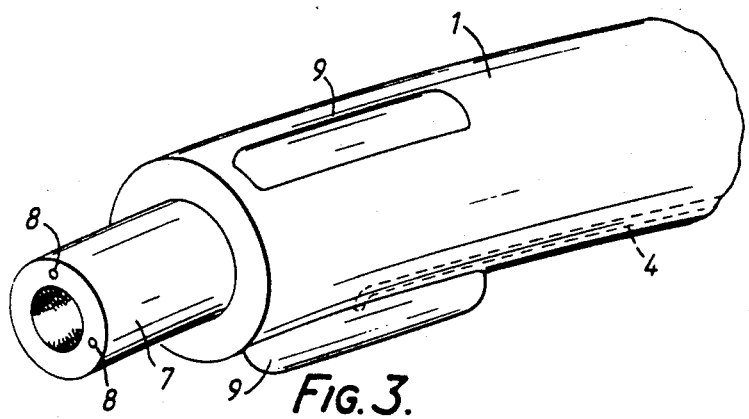
FIG. 3 is a perspective sketch of a second embodiment of catheter, for use in laser surgery.

FIG. 3 illustrates a catheter specifically for use in laser treatment of coronary atheroma. The catheter is of generally similar construction to that of FIGS. 1 and 2, but its main lumen carries a sheathed bundle of optic fibres for transmitting laser light to the site. The sheath 7 may incorporate additional fine lumens 8 for the perfusion of prostacyclin or other platelet-controlling agents, and a dye for staining atheromous material to a colour which makes it susceptible to laser light. These lumens may, of course, alternatively be incorporated through the wall of the catheter.

Further fine lumens corresponding to the lumens 4 of FIG. 1, are provided for controlling wires, as before, for the supply of pressurised gas to a small inflatable sac or sacs 9 carried near the distal end of the catheter. Preferably, these sacs are distributed about the circumference of the catheter. They are individually inflatable (or collapsible) so as to press against the artery wall and thereby permit fairly precise positioning and orientation of the distal end of the catheter and thus of the laser light emitted from it. The sacs may also be abruptly inflated together to disrupt an occlusion.

In a further group of modified catheters, adapted for surgical procedures such as suturing, boring, biopsy sampling and guiding pacemaker wires into position, the catheters are again of the same basic construction, but no lumens are provided for the passage of drugs or other agents to the site. The catheter again incorporates lumens for the control wires and the central lumen is employed for the mechanical control elements to operate tool pieces mounted at the distal end of the catheter.

Figure 4:
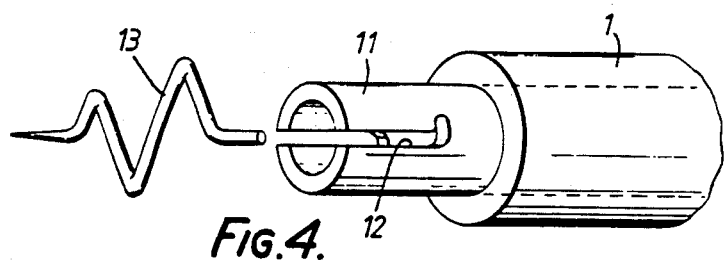
FIG. 4 is a perspective sketch of a third embodiment of catheter, fitted with a suturing device.
Figure 5:
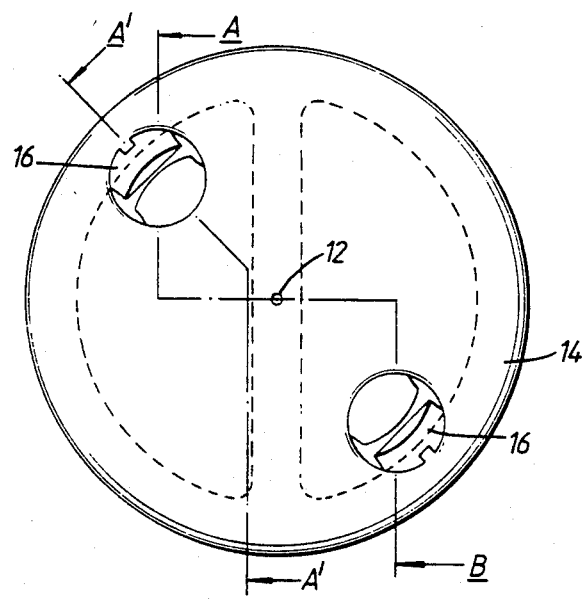
FIG. 5 is a front end view of a fourth embodiment of catheter, fitted with a suturing device.
Figure 6:
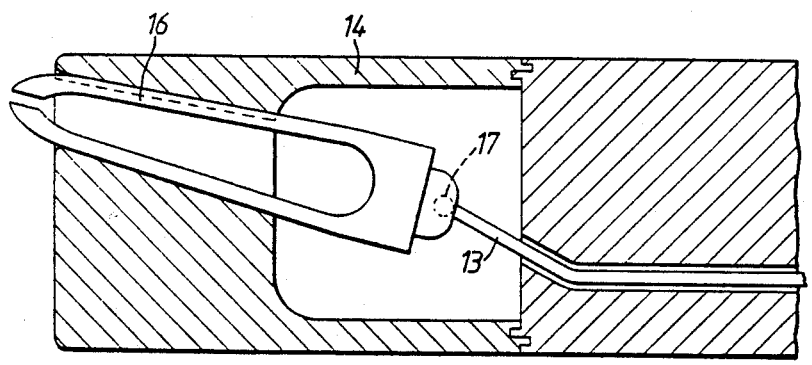
FIGS. 6 and 7 are axial sections on the lines A',A' and A,B respectively, of FIG. 5.
Figure 7:
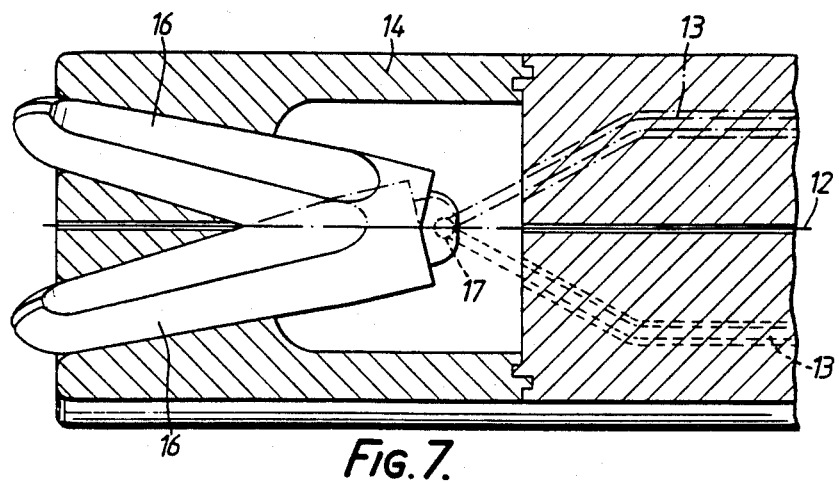

FIG. 4 illustrates such a catheter fitted with a suturing device. The central lumen houses a flexible, torque-transmitting control cable attached to a suture driver 11 of tubular form, having bayonet slots 12 for locating the cross tang 13 of a wire suture of helically spirally form, the helix becoming progressively tighter in a direction away from its pointed leading end. The tang is engaged across the inner ends of the bayonet slots. The suture is applied by pressing it against the site to be stitched and then rotating it, by operation of the control cable, causing the pointed end to penetrate the septal wall (or other muscle or material to be stitched) and with continual rotation the suture is wound progressively into the muscle and concomitantly drawn out of the bayonet slot.

Instead of the suturing device described and illustrated, the same catheter can be fitted with other tool pieces specially adapted for boring, removal of samples for biopsy or the guidance of pacemaker wires.

The catheter shown in FIGS. 5 to 8 is for stitching with a filamentary suture. In this case, the catheter is provided with a small central lumen to receive the suture filament 12 and two further lumens housing control cables 13. Coupled to the distal end of the catheter is a suturing device comprising a generally cup-shaped housing 14 having two through holes in its front wall in which are mounted respective grippers 16. The holes are angled away from each other, and they taper forwardly. The grippers 16 are of a springy material and each has a pair of jaws which are forced together when the gripper is pushed forwardly in its tapered hole. When partially retracted, the jaws spring apart again. The grippers are of generally circular cross-section and are keyed against rotation in their holes. At their rear ends, the grippers are releasably connected as by ball and socket joints 17 to their respective control cables 13.

Figure 8:
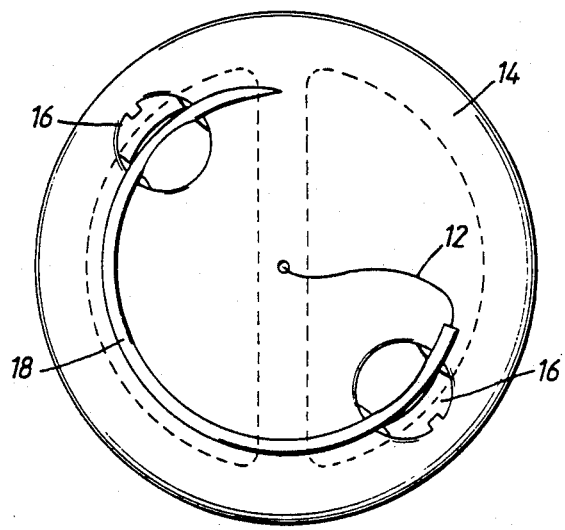
FIG. 8 is a front end view showing a suture needle in position.

Initially, and as shown in FIG. 8, the grippers are both closed against a suture needle 18 attached to the suture filament. The catheter is inserted through a blood vessel to the site to be repaired and suturing is effected by rotation of the head and alternate operation of the grippers to push and pull the needle through the muscle or other tissue to be stitched. The head may be rotatable by a control cable or it may be rotatable within a surrounding sheath extending substantially the full length of the catheter.

I claim:

1. A surgical catheter for use on an patient undergoing nuclear magnetic resonance (NMR) examination, said surgical catheter comprising an elongated element having a distal end and a proximal end; a suturing device located at said distal end of said elongated element, said suturing device comprising a generally cup-shaped housing attached to said distal end, said housing having two openings therein, and two grippers which respectively extend through said two holes in said housing, said gripper including two jaws; and a pair of control elements which extend through said elongated element and are respectively connected to said jaws of each gripper to be alternately opened and closed.

2. A surgical catheter according to claim 1, wherein said element is formed of a plurality of axial segments between said distal end and said proximal end which are composed of materials which material alternate from being highly opaque under NMR examination and less opaque under NMR examination.

3. A surgical catheter according to claim 2, wherein said elongated element provides a primary lumen which extends along the length thereof and is centrally located therewithin and a plurality of additional lumens which extend along the length thereof and are radially outwardly located with respect to said primary lumen.

4. A surgical catheter according to claim 3, wherein said additional lumens are circumferentially spaced around said elongated element and wherein guidance wires are located within said additional lumens to connect said the distal end of said elongated element to facilitate guidance thereof.

5. A surgical catheter according to claim 3, including inflatable sacs located around an exterior of said elongated element near said distal end and wherein said additional lumens communicate with said inflatable sacs so as to enable pressurized fluid to be supplied thereto.

6. A surgical catheter according to claim 3, including a bundle of optical fibers for the transmission of laser light extending through said primary lumen to the distal end of said elongated element.

* * * * *